United States Patent
Andresen et al.

(10) Patent No.: US 10,814,091 B2
(45) Date of Patent: Oct. 27, 2020

(54) SYSTEM FOR DELIVERY OF RESPIRATORY GASES

(71) Applicants: Fisher & Paykel Healthcare Limited, Auckland (NZ); Natalie May Robertson, Auckland (NZ); Jonathan David Harwood, Auckland (NZ)

(72) Inventors: Michael John Andresen, Auckland (NZ); Natalie May Robertson, Auckland (NZ); Jonathan David Harwood, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 925 days.

(21) Appl. No.: 15/031,191

(22) PCT Filed: Oct. 24, 2014

(86) PCT No.: PCT/NZ2014/000223
§ 371 (c)(1),
(2) Date: Apr. 21, 2016

(87) PCT Pub. No.: WO2015/060731
PCT Pub. Date: Apr. 30, 2015

(65) Prior Publication Data
US 2016/0271356 A1    Sep. 22, 2016

Related U.S. Application Data

(60) Provisional application No. 61/895,084, filed on Oct. 24, 2013.

(51) Int. Cl.
*A61M 16/16*    (2006.01)
*A61M 16/08*    (2006.01)
(Continued)

(52) U.S. Cl.
CPC .... *A61M 16/0875* (2013.01); *A61M 16/0003* (2014.02); *A61M 16/109* (2014.02);
(Continued)

(58) Field of Classification Search
CPC ................ A61M 16/16; A61M 16/161; A61M 16/0875; A61M 16/109; A61M 16/1095; A61M 2205/3633
See application file for complete search history.

(56) References Cited

U.S. PATENT DOCUMENTS

| 485,127 A | 10/1892 | Lynch |
| 2,073,335 A | 3/1937 | Connell |

(Continued)

FOREIGN PATENT DOCUMENTS

| AU | 1448473 | 9/1976 |
| AU | 2007317198 A1 | 5/2008 |

(Continued)

OTHER PUBLICATIONS

US 10,426,912 B2, 10/2019, Buswell et al. (withdrawn)
(Continued)

*Primary Examiner* — Timothy A Stanis
(74) *Attorney, Agent, or Firm* — Knobbe, Martens, Olson & Bear, LLP (57) ABSTRACT

A respiratory system provides conditioned respiratory gases to a patient within a controlled temperature environment. A humidification apparatus has an inspiratory tube that may extend to a patient interface. The inspiratory tube may have a reduced length. A thermal insulation component may insulate at least a portion of the inspiratory tube. As a result, less of the inspiratory tube may be exposed to the surrounding ambient environment, which may reduce condensate formation within the inspiratory tube and heat loss to the surrounding ambient environment. The humidification appa-
(Continued)

ratus may be directly coupled to the controlled temperature environment.

18 Claims, 3 Drawing Sheets

(51) Int. Cl.
*A61M 16/10* (2006.01)
*A61M 16/00* (2006.01)

(52) U.S. Cl.
CPC ........ *A61M 16/1095* (2014.02); *A61M 16/16* (2013.01); *A61M 16/161* (2014.02); *A61M 2016/003* (2013.01); *A61M 2016/0039* (2013.01); *A61M 2205/3334* (2013.01); *A61M 2205/3368* (2013.01); *A61M 2205/3633* (2013.01)

(56) References Cited

U.S. PATENT DOCUMENTS

| | | | |
|---|---|---|---|
| 2,516,864 A | 8/1950 | Gilmore et al. |
| 2,788,936 A | 4/1957 | Kemnitz |
| 2,874,722 A | 2/1959 | Hamblin |
| 3,117,596 A | 1/1964 | Khan |
| 3,163,707 A | 12/1964 | Darling |
| 3,283,580 A | 11/1966 | Jacob et al. |
| 3,394,954 A | 7/1968 | Sarns |
| 3,495,628 A | 2/1970 | Boender |
| 3,582,968 A | 6/1971 | Buiting |
| 3,584,193 A | 6/1971 | Badertscher |
| 3,638,926 A | 2/1972 | Melville et al. |
| 3,695,267 A | 10/1972 | Hirtz et al. |
| 3,766,914 A | 10/1973 | Jacobs |
| 3,914,349 A | 10/1975 | Stipanuk |
| 3,926,223 A | 12/1975 | Petzetakis |
| 3,963,856 A | 6/1976 | Carlson et al. |
| 3,990,727 A | 11/1976 | Gallagher |
| 4,013,122 A | 3/1977 | Long |
| 4,013,742 A | 3/1977 | Lang |
| 4,033,808 A | 7/1977 | Petzetakis |
| 4,038,519 A | 7/1977 | Foucras |
| 4,038,980 A | 8/1977 | Fodor |
| 4,051,205 A | 9/1977 | Grant |
| 4,060,576 A | 11/1977 | Grant |
| 4,110,419 A | 8/1978 | Miller |
| 4,111,197 A | 9/1978 | Warncke et al. |
| 4,160,466 A | 7/1979 | Jousson |
| 4,172,105 A | 10/1979 | Miller et al. |
| 4,301,200 A | 11/1981 | Langenfeld |
| 4,333,451 A | 6/1982 | Paluch |
| 4,428,403 A | 1/1984 | Lee et al. |
| 4,430,994 A * | 2/1984 | Clawson ............... A61M 16/16 128/203.27 |
| 4,487,232 A | 12/1984 | Kanao |
| 4,490,575 A | 12/1984 | Kutnyak |
| 4,500,480 A | 2/1985 | Cambio, Jr. |
| 4,529,867 A | 7/1985 | Velnosky et al. |
| 4,531,551 A | 7/1985 | Eichelberger et al. |
| 4,553,023 A | 11/1985 | Jameson et al. |
| 4,574,188 A | 3/1986 | Midgley et al. |
| 4,597,917 A | 7/1986 | Lunsford |
| 4,621,632 A | 11/1986 | Bartels et al. |
| 4,640,804 A | 2/1987 | Mizoguchi |
| 4,676,237 A | 6/1987 | Wood et al. |
| 4,684,786 A | 8/1987 | Mann et al. |
| 4,686,354 A | 8/1987 | Makin |
| 4,695,955 A | 9/1987 | Faisandier |
| 4,708,831 A | 11/1987 | Elsworth et al. |
| 4,710,887 A | 12/1987 | Ho |
| 4,722,334 A | 2/1988 | Blackmer et al. |
| 4,753,758 A | 6/1988 | Miller |
| 4,780,247 A | 10/1988 | Yasuda |
| 4,829,781 A | 5/1989 | Hitzler |
| 4,829,997 A | 5/1989 | Douwens et al. |
| 4,829,998 A | 5/1989 | Jackson |
| 4,844,512 A | 7/1989 | Gahwiler |
| 4,861,523 A | 8/1989 | Beran |
| 4,903,736 A | 2/1990 | Baston et al. |
| 4,911,157 A | 3/1990 | Miller |
| 4,911,357 A | 3/1990 | Kitamura |
| 4,921,642 A | 5/1990 | LaTorraca |
| 4,941,469 A | 7/1990 | Adahan |
| 4,967,744 A | 11/1990 | Chua |
| 5,031,612 A | 7/1991 | Clementi |
| 5,062,145 A | 10/1991 | Zwaan et al. |
| 5,092,326 A | 3/1992 | Winn et al. |
| 5,101,820 A | 4/1992 | Christopher |
| 5,127,442 A | 7/1992 | Blomqvist |
| 5,148,801 A | 9/1992 | Douwens et al. |
| 5,164,652 A | 11/1992 | Johnson et al. |
| 5,213,376 A | 5/1993 | Szabo |
| 5,224,923 A | 7/1993 | Moffett et al. |
| 5,230,331 A | 7/1993 | Rusz et al. |
| 5,231,979 A | 8/1993 | Rose et al. |
| 5,336,156 A | 8/1994 | Miller et al. |
| 5,346,128 A | 9/1994 | Wacker |
| 5,347,211 A | 9/1994 | Jakubowski |
| 5,367,604 A | 11/1994 | Murray |
| 5,388,443 A | 2/1995 | Manaka |
| 5,392,770 A | 2/1995 | Clawson et al. |
| 5,404,729 A | 4/1995 | Matsuoka et al. |
| 5,405,269 A | 4/1995 | Stupecky |
| 5,428,752 A | 6/1995 | Goren et al. |
| 5,449,234 A | 9/1995 | Gipp et al. |
| 5,454,061 A | 9/1995 | Carlson |
| 5,482,031 A | 1/1996 | Lambert |
| 5,516,466 A | 5/1996 | Schlesch et al. |
| 5,529,060 A | 6/1996 | Salmon et al. |
| 5,537,996 A | 7/1996 | McPhee |
| 5,551,731 A | 9/1996 | Gray et al. |
| 5,558,084 A | 9/1996 | Daniell et al. |
| 5,564,415 A | 10/1996 | Dobson et al. |
| 5,588,423 A | 12/1996 | Smith |
| 5,591,292 A | 1/1997 | Blomqvist |
| 5,600,752 A | 2/1997 | Lopatinsky |
| 5,630,806 A | 5/1997 | Inagaki |
| 5,637,168 A | 6/1997 | Carlson |
| 5,640,951 A | 6/1997 | Huddart et al. |
| 5,673,687 A | 10/1997 | Dobson et al. |
| 5,759,149 A | 6/1998 | Goldberg et al. |
| 5,769,071 A | 6/1998 | Turnbull |
| 5,778,872 A | 7/1998 | Fukunaga et al. |
| 5,848,223 A | 12/1998 | Carlson |
| 5,906,201 A | 5/1999 | Nilson |
| 5,943,473 A | 8/1999 | Levine |
| 5,988,164 A | 11/1999 | Paluch |
| 5,991,507 A | 11/1999 | Bencsits |
| 6,010,118 A | 1/2000 | Milewicz |
| 6,024,694 A | 2/2000 | Goldberg et al. |
| 6,038,457 A | 3/2000 | Barkat |
| 6,050,260 A | 4/2000 | Daniell et al. |
| 6,078,730 A | 6/2000 | Huddart et al. |
| 6,095,505 A | 8/2000 | Miller |
| 6,105,649 A | 8/2000 | Levingston et al. |
| 6,109,782 A | 8/2000 | Fukura et al. |
| 6,125,847 A | 10/2000 | Lin |
| 6,138,674 A | 10/2000 | Gull et al. |
| 6,142,974 A | 11/2000 | Kistner et al. |
| 6,158,431 A | 12/2000 | Poole |
| 6,167,883 B1 | 1/2001 | Beran et al. |
| 6,189,870 B1 | 2/2001 | Withall |
| 6,190,480 B1 | 2/2001 | Carlson |
| 6,219,490 B1 | 4/2001 | Gibertoni et al. |
| 6,272,933 B1 | 8/2001 | Gradon et al. |
| 6,311,958 B1 | 11/2001 | Stanek |
| 6,347,646 B2 | 2/2002 | Fukui et al. |
| 6,349,722 B1 | 2/2002 | Gradon et al. |
| 6,367,472 B1 | 4/2002 | Koch |
| 6,367,510 B1 | 4/2002 | Carlson |
| 6,374,864 B1 | 4/2002 | Philip |
| 6,384,755 B1 | 5/2002 | Hayden |
| 6,394,084 B1 | 5/2002 | Nitta |

(56) References Cited

U.S. PATENT DOCUMENTS

| | | |
|---|---|---|
| 6,394,145 B1 | 5/2002 | Bailly |
| 6,397,841 B1 | 6/2002 | Kenyon et al. |
| 6,397,846 B1 | 6/2002 | Skog et al. |
| 6,398,197 B1 | 6/2002 | Dickinson et al. |
| 6,463,925 B2 | 10/2002 | Nuckols et al. |
| 6,474,335 B1 | 11/2002 | Lammers |
| 6,537,405 B1 | 3/2003 | Henderson et al. |
| 6,540,734 B1 | 4/2003 | Chiu et al. |
| 6,543,412 B2 | 4/2003 | Amou et al. |
| 6,564,011 B1 | 5/2003 | Janoff et al. |
| 6,584,972 B2 | 7/2003 | McPhee |
| 6,594,366 B1 | 7/2003 | Adams |
| 6,668,828 B1 | 12/2003 | Figley et al. |
| 6,691,707 B1 | 2/2004 | Gunaratnam et al. |
| 6,694,974 B1 | 2/2004 | George-Gradon et al. |
| 6,718,974 B1 | 4/2004 | Moberg |
| 6,827,109 B2 | 12/2004 | Mccaughtry |
| 6,918,389 B2 | 7/2005 | Seakins et al. |
| 6,932,119 B2 | 8/2005 | Carlson |
| 6,953,354 B2 | 10/2005 | Edirisuriya et al. |
| 7,086,422 B2 | 8/2006 | Kressierer et al. |
| 7,096,864 B1 | 8/2006 | Mayer et al. |
| 7,120,354 B2 | 10/2006 | Mackie et al. |
| 7,156,127 B2 | 1/2007 | Moulton et al. |
| 7,157,035 B2 | 1/2007 | Edirisuriya et al. |
| 7,291,240 B2 | 11/2007 | Smith et al. |
| 7,468,116 B2 | 12/2008 | Smith et al. |
| 7,588,029 B2 | 9/2009 | Smith et al. |
| 7,588,186 B2 | 9/2009 | Steffen et al. |
| 7,637,288 B2 | 12/2009 | Huber et al. |
| 7,647,926 B2 | 1/2010 | Gerder et al. |
| 7,766,050 B2 | 8/2010 | Patel |
| 7,814,907 B2 * | 10/2010 | Bremner ........... A61M 16/0816 128/203.26 |
| 7,965,930 B2 | 6/2011 | Carlson et al. |
| 7,997,267 B2 | 8/2011 | Ging et al. |
| 8,091,547 B2 | 1/2012 | Thudor et al. |
| 8,122,882 B2 | 2/2012 | Mcghin et al. |
| 8,186,345 B2 | 5/2012 | Payton et al. |
| 8,235,041 B2 | 8/2012 | Seakins et al. |
| 8,333,194 B2 | 12/2012 | Lewis et al. |
| 8,333,199 B2 | 12/2012 | Landis et al. |
| 8,360,059 B2 | 1/2013 | Koulechov et al. |
| 8,453,641 B2 | 6/2013 | Payton et al. |
| 8,459,259 B2 | 6/2013 | Klasek et al. |
| 8,469,025 B2 | 6/2013 | Mayer et al. |
| 8,522,782 B2 | 9/2013 | Lewis et al. |
| 8,563,863 B2 | 10/2013 | Carlson |
| 8,563,864 B2 | 10/2013 | Carlson |
| 8,631,789 B2 | 1/2014 | Virr et al. |
| 8,709,187 B2 | 4/2014 | Smith et al. |
| 8,733,349 B2 | 5/2014 | Bath et al. |
| 8,844,522 B2 | 9/2014 | Huby et al. |
| 9,119,933 B2 | 9/2015 | Bedford et al. |
| 9,440,040 B2 | 9/2016 | Klasek et al. |
| 9,517,321 B2 | 12/2016 | Buechi et al. |
| 9,555,210 B2 | 1/2017 | Seakins et al. |
| 9,572,949 B2 | 2/2017 | Vos et al. |
| 9,855,398 B2 | 1/2018 | Klasek et al. |
| 10,080,866 B2 | 9/2018 | Stoks et al. |
| 2001/0017134 A1 | 8/2001 | Bahr |
| 2001/0050080 A1 | 12/2001 | Seakins et al. |
| 2002/0038392 A1 | 3/2002 | De La Huerga |
| 2002/0120236 A1 | 8/2002 | Diaz et al. |
| 2002/0124847 A1 | 9/2002 | Smith et al. |
| 2002/0173717 A1 | 11/2002 | Rohling et al. |
| 2002/0186966 A1 | 12/2002 | Zimmer et al. |
| 2003/0059213 A1 | 3/2003 | Mackie et al. |
| 2003/0183294 A1 | 10/2003 | Carlson |
| 2003/0236015 A1 | 12/2003 | Edirisuriya et al. |
| 2004/0074493 A1 | 4/2004 | Seakins et al. |
| 2004/0074495 A1 | 4/2004 | Wickham et al. |
| 2004/0079371 A1 | 4/2004 | Gray |
| 2004/0081784 A1 | 4/2004 | Smith et al. |
| 2004/0099268 A1 | 5/2004 | Smith et al. |
| 2004/0101026 A1 | 5/2004 | Nitta et al. |
| 2004/0149284 A1 | 8/2004 | Smith et al. |
| 2004/0182392 A1 | 9/2004 | Gerder et al. |
| 2004/0244858 A1 | 12/2004 | Jeong |
| 2005/0059957 A1 | 6/2005 | Byerly et al. |
| 2005/0152733 A1 | 7/2005 | Marchan |
| 2006/0165829 A1 | 7/2006 | Smith et al. |
| 2006/0283447 A1 | 12/2006 | Dhuper et al. |
| 2007/0047733 A1 | 3/2007 | Bremer et al. |
| 2007/0051368 A1 | 3/2007 | Seakins et al. |
| 2007/0079982 A1 | 4/2007 | Laurent et al. |
| 2007/0107737 A1 | 5/2007 | Landis et al. |
| 2007/0277828 A1 | 12/2007 | Ho et al. |
| 2008/0078259 A1 | 4/2008 | Duff |
| 2008/0105257 A1 | 5/2008 | Klasek et al. |
| 2008/0173305 A1 | 7/2008 | Frater |
| 2008/0202512 A1 | 8/2008 | Kressierer et al. |
| 2008/0251073 A1 | 10/2008 | Jassell et al. |
| 2008/0264413 A1 | 10/2008 | Doherty et al. |
| 2009/0078259 A1 | 3/2009 | Kooij et al. |
| 2009/0078440 A1 | 3/2009 | Carlson et al. |
| 2009/0110379 A1 | 4/2009 | McGhin et al. |
| 2009/0126817 A1 | 5/2009 | Gray |
| 2009/0149696 A1 | 6/2009 | Chilton, III |
| 2009/0320840 A1 | 12/2009 | Klasek et al. |
| 2010/0083965 A1 | 4/2010 | Virr et al. |
| 2010/0116272 A1 | 5/2010 | Row et al. |
| 2010/0224276 A1 | 9/2010 | Forrester et al. |
| 2011/0023874 A1 | 2/2011 | Bath et al. |
| 2011/0046494 A1 | 2/2011 | Balji et al. |
| 2011/0155132 A1 | 6/2011 | Virr et al. |
| 2011/0168287 A1 | 7/2011 | Carlson |
| 2012/0125333 A1 | 5/2012 | Bedford |
| 2012/0255758 A1 | 10/2012 | Lee |
| 2013/0104888 A1 | 5/2013 | Landis et al. |
| 2013/0104901 A1 | 5/2013 | Landis et al. |
| 2013/0174839 A1 | 7/2013 | Ging et al. |
| 2013/0239966 A1 | 9/2013 | Klasek et al. |
| 2013/0255677 A1 | 10/2013 | Varga |
| 2013/0280055 A1 | 10/2013 | Daly et al. |
| 2013/0340752 A1 | 12/2013 | Landis et al. |
| 2014/0037276 A1 | 2/2014 | Carlson |
| 2014/0130802 A1 | 5/2014 | Virr et al. |
| 2014/0202460 A1 | 7/2014 | Bath et al. |
| 2014/0216459 A1 | 8/2014 | Vos et al. |
| 2014/0246021 A1 | 9/2014 | Buechi et al. |
| 2014/0311487 A1 | 10/2014 | Buechi et al. |
| 2014/0318536 A1 | 10/2014 | Landis et al. |
| 2014/0366876 A1 | 12/2014 | Huby et al. |
| 2015/0090260 A1 | 4/2015 | Seakins et al. |
| 2015/0306333 A1 | 10/2015 | Amadio et al. |
| 2016/0256657 A1 | 9/2016 | Klasek et al. |
| 2016/0271356 A1 | 9/2016 | Robertson et al. |
| 2016/0354573 A1 | 12/2016 | Buswell et al. |
| 2017/0100556 A1 | 4/2017 | Munkelt et al. |
| 2018/0280651 A1 | 10/2018 | Liu et al. |
| 2019/0076620 A1 | 3/2019 | Stoks et al. |
| 2020/0016361 A1 | 1/2020 | Buswell et al. |

FOREIGN PATENT DOCUMENTS

| | | |
|---|---|---|
| CN | 2243015 Y | 12/1996 |
| CN | 1549910 | 11/2004 |
| CN | 201672170 U | 12/2010 |
| DE | 36 29 353 | 1/1988 |
| DE | 4020522 A | 1/1992 |
| DE | 40 34 611 | 5/1992 |
| DE | 4102223 A1 | 7/1992 |
| DE | 9200567 U1 | 7/1992 |
| DE | 33 11 811 | 10/1994 |
| DE | 94 09 231.1 | 12/1994 |
| DE | 19647548 A1 | 5/1998 |
| DE | 19958296 C1 | 9/2001 |
| DE | 20202906 U1 | 5/2002 |
| DE | 10312881 B3 | 5/2004 |
| DE | 20 2004 006 484 U1 | 9/2005 |
| DE | 202005008156 U1 | 11/2006 |
| DE | 20 2006 007 397 | 9/2007 |
| DE | 202006007397 U1 | 9/2007 |

(56) References Cited

FOREIGN PATENT DOCUMENTS

| | | |
|---|---|---|
| DE | 102006056781 A1 | 6/2008 |
| DE | 102007003454 | 7/2008 |
| DE | 102007003455 | 8/2008 |
| DE | 202007018764 U1 | 6/2009 |
| DE | 102011055439 A1 | 5/2013 |
| EP | 0111248 A2 | 6/1984 |
| EP | 0201985 | 11/1986 |
| EP | 0232864 A2 | 8/1987 |
| EP | 0 258 928 | 9/1988 |
| EP | 0342802 | 11/1989 |
| EP | 0 481 459 | 4/1992 |
| EP | 0 556 561 | 8/1993 |
| EP | 616 166 | 9/1994 |
| EP | 0621050 A2 | 10/1994 |
| EP | 0672430 A2 | 9/1995 |
| EP | 0 885 623 | 12/1998 |
| EP | 0956068 | 11/1999 |
| EP | 1078645 | 2/2001 |
| EP | 1127583 | 8/2001 |
| EP | 1 138 341 | 10/2001 |
| EP | 1145678 | 10/2001 |
| EP | 1147004 B1 | 2/2003 |
| EP | 1380276 A | 1/2004 |
| EP | 1380276 A1 | 1/2004 |
| EP | 1396277 A2 | 3/2004 |
| EP | 1535722 A2 | 6/2005 |
| EP | 1579984 A2 | 9/2005 |
| EP | 2075026 A1 | 7/2009 |
| EP | 2079505 | 7/2009 |
| EP | 2269680 A1 | 1/2011 |
| EP | 2133611 B1 | 9/2011 |
| EP | 2269680 | 9/2012 |
| EP | 2269680 A | 9/2012 |
| EP | 2514478 | 7/2013 |
| EP | 2689174 | 1/2014 |
| EP | 2337604 | 3/2014 |
| GB | 1 167 551 | 10/1969 |
| GB | 2056611 | 3/1981 |
| GB | 2173274 A | 2/1986 |
| GB | 2 277 689 | 11/1994 |
| JP | S56-109189 U | 8/1981 |
| JP | S59-113392 | 6/1984 |
| JP | 05-317428 | 12/1993 |
| JP | 08-061731 | 3/1996 |
| JP | H08-109984 A | 4/1996 |
| JP | H09-234247 | 9/1997 |
| JP | H09-276408 | 10/1997 |
| JP | H11-033119 A | 2/1999 |
| JP | H11-286058 A | 10/1999 |
| JP | 2001-129091 | 5/2001 |
| JP | 2001-511507 A | 8/2001 |
| JP | 2003-139276 A | 5/2003 |
| JP | 2004-148817 | 5/2004 |
| JP | 4422293 B2 | 2/2010 |
| NZ | 579384 | 5/2011 |
| NZ | 587113 | 12/2011 |
| NZ | 589766 | 5/2012 |
| NZ | 575837 | 7/2012 |
| NZ | 583968 | 10/2012 |
| NZ | 590924 | 8/2013 |
| NZ | 600986 | 8/2013 |
| NZ | 597179 | 9/2013 |
| NZ | 597827 | 6/2014 |
| NZ | 605324 | 6/2014 |
| NZ | 605326 | 7/2014 |
| NZ | 607629 | 7/2014 |
| NZ | 610299 | 11/2014 |
| NZ | 701541 | 5/2015 |
| NZ | 625795 | 6/2015 |
| NZ | 620739 | 8/2015 |
| NZ | 625605 | 4/2016 |
| NZ | 710351 | 1/2017 |
| NZ | 631008 | 7/2017 |
| SU | 379270 | 4/1973 |
| WO | WO 92/21163 A1 | 11/1992 |
| WO | WO 1996/020748 A1 | 7/1996 |
| WO | WO 97/18001 A1 | 5/1997 |
| WO | WO 98/26826 | 6/1998 |
| WO | WO 01/10489 | 2/2001 |
| WO | WO 02/32486 | 4/2002 |
| WO | WO 2003/022342 A1 | 3/2003 |
| WO | WO 2003/026721 A2 | 4/2003 |
| WO | WO 2004/024429 A1 | 3/2004 |
| WO | WO 2004/039444 A1 | 5/2004 |
| WO | WO 2004/105847 | 12/2004 |
| WO | WO 2004/105848 A1 | 12/2004 |
| WO | WO 2005/021076 A2 | 3/2005 |
| WO | WO 2006/092001 A1 | 9/2006 |
| WO | WO 2006/095151 | 9/2006 |
| WO | WO 2007/051230 A1 | 5/2007 |
| WO | WO 2008/055308 A1 | 5/2008 |
| WO | WO 2008/060046 A1 | 5/2008 |
| WO | WO 2008/060295 | 5/2008 |
| WO | WO 2008/076230 | 6/2008 |
| WO | WO 2009/015410 A1 | 2/2009 |
| WO | WO 2009/022004 A2 | 2/2009 |
| WO | WO 2010/084183 A2 | 7/2010 |
| WO | WO 2011/051837 A1 | 5/2011 |
| WO | WO 2011/051870 A1 | 5/2011 |
| WO | WO 2011/136665 A1 | 11/2011 |
| WO | WO 2011/162622 A1 | 12/2011 |
| WO | WO 2012/053910 A1 | 4/2012 |
| WO | WO 2012/164407 A1 | 12/2012 |
| WO | WO 2013/045575 | 4/2013 |
| WO | WO 2013/127474 | 9/2013 |
| WO | WO 2013/137753 A1 | 9/2013 |
| WO | WO 2013/147623 A1 | 10/2013 |
| WO | WO 2013/165263 A1 | 11/2013 |
| WO | WO 2014/025266 | 2/2014 |
| WO | WO 2014/077706 A1 | 5/2014 |
| WO | WO 2014/088430 A1 | 6/2014 |
| WO | WO 2014/205513 | 12/2014 |
| WO | WO 2015/038013 A1 | 3/2015 |
| WO | WO 2015/142192 | 9/2015 |
| WO | WO 2017/043981 A1 | 3/2017 |
| WO | WO 2018/116187 | 6/2018 |

OTHER PUBLICATIONS

International Search Report; PCT/NZ2014/000223; dated Mar. 13, 2015, 9 pages.
MR810 Respiratory Humidifier Technical Manual, Revision C.
Fisher & Paykel Healthcare, Annual Report 2003.
Fisher & Paykel Healthcare, FY04 Full Year Overview & Update, May 24, 2004.
Fisher & Paykel Healthcare, Full Year Analyst Briefing, Jun. 5, 2002.
MR850 Respiratory Humidifier Instruction Sheet, Rev. G, Feb. 2004.

* cited by examiner

SYSTEM FOR DELIVERY OF RESPIRATORY GASES

CROSS REFERENCE TO RELATED APPLICATIONS

The present application claims priority benefit of the U.S. Provisional Application having the title DELIVERY OF RESPIRATORY GASES Ser. No. 61/895,084, filed on Oct. 24, 2013, which is hereby incorporated by reference in its entirety.

BACKGROUND

Technical Field

The present disclosure generally relates to the delivery of humidified gases to a patient. More particularly, the present disclosure relates to a tube system for delivery of humidified gases to a patient within a controlled temperature environment.

Description of the Related Art

A humidification apparatus is used to provide heated and humidified respiratory gases to a patient via a patient interface. Respiratory gases delivered to a patient at 100% relative humidity and 37° C. mimic the transformation of air that occurs as the respiratory gases pass through the nose to the lungs. This may promote efficient gas exchange and ventilation in the lungs, aid defense mechanisms in the airways and increase patient comfort during treatment.

Some patients may require treatment within a controlled temperature environment, such as, for example, an incubator. Such an environment may reduce heat and water loss in the patients by aiming to maintain a core temperature of approximately 36.5-37.2° C. Respiratory gases may be delivered to the patients within the controlled temperature environment via a respiratory assistance system comprising a gases source, a humidification apparatus and a tube system. Multiple tubes may be used to compensate for temperature differences between the controlled temperature environment and the surrounding ambient environment.

SUMMARY

Although the prior art comprises respiratory assistance systems wherein conditioned respiratory gases may be delivered to a patient in a controlled temperature environment, an aspect of at least one of the embodiments disclosed herein includes the realisation that there are problems with the respiratory assistance systems of the prior art.

A respiratory assistance system may struggle to compensate for the temperature differences observed between the controlled temperature environment and the surrounding ambient conditions. This may cause condensate to occur within the inspiratory tube of the respiratory assistance system, which may impact the treatment.

Prior art tube systems may comprise a single heated tube that extends from the humidification apparatus to the patient via the controlled temperature environment. This may result in a tube that is exposed to two different environments: the controlled temperature environment and the surrounding ambient environment. The region of the tube exposed to the controlled temperature environment may be heated in addition to the tube heating mechanisms, which may result in an undesirably elevated temperature of the respiratory gases delivered to the patient. This may result in difficulties in maintaining a desirable temperature and/or humidity level of the respiratory gases at the patient end. The region of the tube exposed to the surrounding ambient environment may have increased heat loss and thus may have increased condensate formation within the tube.

Alternatively, some prior art tube systems may comprise a single unheated tube that extends from the humidification apparatus to the patient via the controlled temperature environment. Condensate may form along the length of the tube as the heated and humidified gases enter the unheated tube which is exposed to the surrounding ambient environment.

Other prior art tube systems may comprise multiple tubes, wherein one tube may be heated and one tube may be unheated. The heated tube may be connected between the humidification apparatus and the unheated tube. The unheated tube can be added as an extension from the heated tube, connecting to the patient interface. As a result, the unheated tube may be configured to be located within the controlled temperature environment. However, this system may rely on correct setup and positioning of the tubes to reduce the amount of condensate within the system. The steps to correctly identify and set up the tube system may prove to be complicated and time consuming for a user. Incorrect setup may lead to a part of the unheated tube being positioned such that it is exposed to the surrounding ambient environment or may lead to a part of the heated tube being positioned within the controlled temperature environment. An exposed part of the unheated tube to the controlled temperature environment may result in heat loss and condensate formation within the unheated tube, whereas positioning a part of the heated tube within the controlled temperature environment may lead to inaccurate heating of the heated tube, which may result in the respiratory gases being delivered to the patient at a less desirable temperature or humidity level.

In some embodiments, the tube system may comprise a temperature sensor at the patient end of the heated tube to provide feedback to the humidification apparatus. As a result, the temperature of the respiratory gases that are delivered to the patient may be highly dependent on the correct placement of the temperature sensor. Incorrect setup of the tube system may result in the temperature sensor being located within the controlled temperature environment, which may thus not generate accurate or predictable representations of the temperature at the entrance to the controlled temperature environment. In some cases, this may cause elevated readings to occur, thereby resulting in compensation of the humidification apparatus for these readings. This may result in provision of respiratory gases with a decreased temperature or humidity to the patient.

In such prior art systems, the humidification apparatus may be positioned proximal to the gases source. Thus, the length of the tube system as spanned between the humidification apparatus and the patient may be substantial.

A system is disclosed which provides an improved respiratory assistance system to be used within a controlled temperature environment.

In some embodiments, the humidification apparatus may be mounted at or proximal to a periphery of the controlled temperature environment. This may minimise the length of the inspiratory tube between the humidification apparatus and the controlled temperature environment. As a result, only a very small part of the inspiratory tube may be exposed to the surrounding ambient environment. In some embodiments, the inspiratory tube may be an unheated tube. In some embodiments, the inspiratory tube may comprise a thermally insulating component, for example, an insulating sleeve, cover or outer tube.

In some embodiments, the length of the gases supply tube may be extended such that it compensates for the decreased length of the inspiratory tube, while maintaining an overall length that is comparable to that of prior art systems. This may cause the compressible volume of the system to be maintained, while both improving the flexibility of the system and reducing the condensate within the system. In some embodiments, a sensor may be located at the patient end of the inspiratory tube which may be used individually or in combination with a second sensor at the humidification apparatus to provide feedback regarding a characteristic of the respiratory gases flow being delivered to the patient. This may result in more accurate control of the condition of the respiratory gases delivered to the patient. In some embodiments, a temperature sensor may be used which may allow more accurate control of the temperature of the respiratory gases delivered to the patient. In some embodiments, this may result in use of a lower duty cycle to sufficiently heat and humidify the gases to be delivered to the patient.

Some embodiments may couple the humidification apparatus to the controlled temperature environment. The humidification apparatus or components of the humidification apparatus such as the humidification chamber may be modified to couple with the controlled temperature environment. As a result, the likelihood or extent of exposure of the inspiratory tube to the surrounding ambient environment may be reduced, which may lead to a reduction in heat loss and condensate formation within the inspiratory tube. In some embodiments, this may result in a lower duty cycle to sufficiently heat and humidify the gases to be delivered to the patient. Consumable costs may be reduced which may lead to a reduction in the overall cost of the respiratory assistance system.

According to a first aspect of the disclosure, there is provided a respiratory assistance system that may comprise a humidification apparatus and a tube system. The humidification apparatus may be configured to condition respiratory gases and may comprise a humidification chamber configured to hold a volume of liquid. The tube system may comprise a gases supply tube and an inspiratory tube. The gases supply tube may be configured to extend between the gases source and the humidification apparatus and to transport respiratory gases from the gases source to the humidification apparatus. The inspiratory tube may be configured to transport the conditioned respiratory gases from the humidification apparatus to a patient. A first region of the inspiratory tube may be configured to be at least partially positioned within a controlled temperature environment. A second region of the inspiratory tube may be configured to be at least partially positioned outside of the controlled temperature environment and in a surrounding ambient environment. At least a part of the inspiratory tube that is positioned outside of the controlled temperature environment may comprise a thermal insulation component configured to insulate the inspiratory tube.

The thermal insulation component may be configured to insulate the entire second region of the inspiratory tube that is positioned outside of the controlled temperature region.

The thermal insulation component may compress or expand in length to compensate for a change in length of the second region of the inspiratory tube.

The length of the gases supply tube may be 1 m-1.5 m.

The inspiratory tube may comprise a first length and the gases supply tube may comprise a second length. A desired compressible volume of the tube system may be known, from which a total length of the tube system can be calculated. The sum of the first length and the second length may equal the calculated total length.

The length of the inspiratory tube may be 500 mm to 600 mm.

The controlled temperature environment may comprise a periphery or edge, and the humidification apparatus may be coupled to the periphery or edge of the controlled temperature environment.

The inspiratory tube may comprise a first end and a second end, and the humidification chamber may comprise a body and an outlet port that may be configured to couple the first end of the inspiratory tube closer to the body of the humidification chamber.

The respiratory assistance system may comprise a sensor configured to detect a characteristic of the respiratory gases flow.

The sensor may be configured to detect a temperature of the respiratory gases flow.

The sensor may comprise a temperature sensor.

The sensor may be configured to detect a humidity of the respiratory gases flow.

The sensor may comprise a humidity sensor.

The sensor may be configured to detect a flow rate of the respiratory gases flow.

The sensor may comprise a flow sensor.

The inspiratory tube may comprise a first end and a second end, the first end of the inspiratory tube may be closer to an outlet portion of the humidification chamber than the second end of the inspiratory tube, and the sensor may be located at one of the first end of the inspiratory tube or an outlet port of a humidification chamber of the humidification apparatus.

The inspiratory tube may comprise a first end and a second end, and a second sensor may be located at the second end of the inspiratory tube.

The thermal insulation component may comprise a concertina tube.

The inspiratory tube may comprise a first end and a second end, and the thermal insulation component may be fixed at the first end of the inspiratory tube.

A fluid gap may exist between the thermal insulation component and the inspiratory tube.

The fluid gap may comprise a liquid.

The fluid gap may comprise a gas, such as air.

The controlled temperature environment may comprise a periphery or edge, and the thermal insulation component may be configured to releasably couple with the periphery or edge of the controlled temperature environment via a coupling mechanism.

The coupling mechanism may comprise a magnetic structure.

The full length of the inspiratory tube may be configured to be positioned within the controlled temperature environment.

The inspiratory tube may be heated.

According to a second aspect of the disclosure, there is provided a tube system configured for use in a respiratory assistance system, where the tube system may comprise a gases supply tube, an inspiratory tube, and a thermal insulation component. The gases supply tube may be configured to extend between a gases source and a humidification apparatus and may be configured to transport respiratory gases from the gases source to the humidification apparatus. The inspiratory tube may be configured to couple between the humidification apparatus and a patient interface, and may be configured to transport respiratory gases from the humidification apparatus to a patient. The thermal insulation component may be configured to insulate at least a part of the inspiratory tube. The inspiratory tube may comprise a first end and a second end and may comprise a heating mechanism configured to heat the respiratory gases within the inspiratory tube. The tube system may comprise a sensor to determine a characteristic of the respiratory gases flow in the inspiratory tube. The sensor may be configured to provide feedback to a control system within the humidification apparatus, and the feedback may be used to control a duty cycle of a heating element of the humidification apparatus.

The inspiratory tube may be configured to be at least partially positioned within the controlled temperature environment.

The inspiratory tube may comprise a first region and a second region. The first region may be configured to be at least partially positioned in the controlled temperature environment. The second region may be configured to be at least partially positioned in a surrounding ambient environment.

The thermal insulation component may be configured to insulate the second region of the inspiratory tube.

The thermal insulation component may compress or expand in length to compensate for a change in length of the second region of the inspiratory tube.

The length of the gases supply tube may be 1 m-1.5 m.

The inspiratory tube may comprise a first length and the gases supply tube may comprise a second length. A desired compressible volume of the tube system may be known, from which a total length of the tube system may be calculated. The sum of the first length and the second length may equal the calculated total length.

The length of the inspiratory tube may be 500 mm to 600 mm.

The controlled temperature environment may comprise a periphery or edge, and the humidification apparatus may be coupled to the periphery or edge of the controlled temperature environment.

The inspiratory tube may comprise a first end and a second end, and the humidification chamber may comprise a body and an outlet port that may be configured to couple the first end of the inspiratory tube closer to the body of the humidification chamber.

The sensor may be configured to detect a temperature of the respiratory gases flow.

The sensor may be a temperature sensor.

The sensor may be configured to detect a humidity of the respiratory gases flow.

The sensor may be a humidity sensor.

The sensor may be configured to detect a flow rate of the respiratory gases flow.

The sensor may be a flow sensor.

The inspiratory tube may comprise a first end and a second end, and the sensor may be located at one of the first end of the inspiratory tube or an outlet port of a humidification chamber of the humidification apparatus.

The inspiratory tube may comprise a first end and a second end, and a second sensor may be located at the second end of the inspiratory tube.

The thermal insulation component may comprise a concertina tube.

The inspiratory tube may comprise a first end and a second end, and the thermal insulation component may be fixed at the first end of the inspiratory tube.

A fluid gap may exist between the thermal insulation component and the inspiratory tube.

The fluid gap may comprise a liquid.

The fluid gap may comprise a gas, such as air.

The controlled temperature environment may comprise a periphery or edge, and the thermal insulation component may be configured to releasably couple with the periphery or edge via a coupling mechanism.

The coupling mechanism may comprise a magnetic structure.

The full length of the inspiratory tube may be configured to be positioned within the controlled temperature environment.

The inspiratory tube may be heated.

According to a third aspect of the disclosure, there is provided a method of using a humidification apparatus in a respiratory assistance system. The method comprises positioning an inspiratory tube near a controlled temperature environment, wherein the inspiratory tube may be configured to transport respiratory gases from a humidification apparatus to a patient interface and may comprise a first region positioned in a surrounding ambient environment and a second region positioned in the controlled temperature environment; adjusting a thermal insulation component coupled to the inspiratory tube such that the first region of the inspiratory tube is at least partially insulated by the thermal insulation component; and using a sensor to determine a characteristic of the respiratory gases flow.

BRIEF DESCRIPTION OF THE DRAWINGS

These and other features, aspects, and advantages of the present disclosure will be described with respect to the following figures, which are intended to illustrate and not to limit the preferred embodiments.

DETAILED DESCRIPTION

A gases source as herein described may refer to a source of respiratory gases for example, a ventilator, blower or wall source.

A humidification apparatus as herein described may refer to an apparatus that heats and humidifies respiratory gases. It may comprise a control system, a heating apparatus, and a humidification chamber. In some embodiments, the humidification apparatus may also comprise a gases source. In some embodiments, the gases source may be an integral part of the humidification apparatus.

A tube system may comprise both an inspiratory tube and an expiratory tube or, in some embodiments, the tube system may comprise only an inspiratory tube. The inspiratory tube may comprise multiple tubes. In some embodiments, at least one of the tubes or tube components may be heated.

A patient interface as herein described may refer to any component used to connect the tube system to the patient and may refer to a nasal cannula, nasal pillows, full face mask, oral mask, nasal mask, endotracheal tube or tracheal mask. The patient interface may be used for patients treated invasively or non-invasively.

A controlled temperature environment as herein described may refer to an environment that is configured to at least partially modify the temperature of a patient, for example, but not limited to, an incubator, an infant warmer or a blanket. The controlled temperature environment comprises a periphery. As used herein, periphery has its ordinary meaning and also means "outer limits or edge of an area or object" and periphery may refer to a side of a housing, a wall, an edge or a boundary.

Respiratory Assistance System

Figure 1:
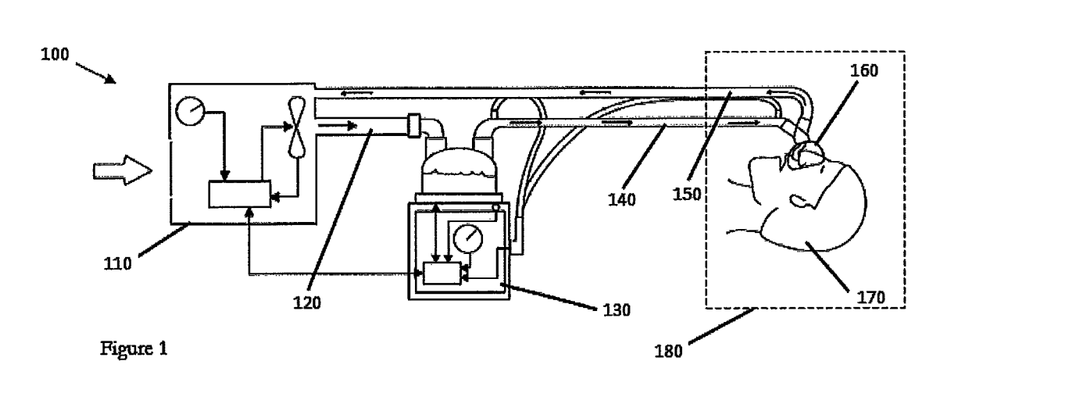
FIG. 1 is a schematic view of an example embodiment of a respiratory assistance system.

FIG. 1 is a schematic view of an example respiratory assistance system 100. The respiratory assistance system 100 can be used to provide respiratory gases to a patient 170. The respiratory assistance system 100 may comprise a gases source 110. The gases source can deliver gases to a humidification apparatus 130. In some configurations, the gases source can deliver gases to the humidification apparatus 130 through a gases supply tube 120.

The humidification apparatus 130 may humidify the respiratory gases. In some configurations, the humidification apparatus 130 can heat and humidify the respiratory gases. The humidification apparatus 130 may comprise a humidification chamber 135. In some configurations, the humidification chamber 135 can be configured to hold a liquid.

In some configurations, a tube system may deliver the respiratory gases to or from the patient 170. In some configurations, a patient interface 160 can be used to deliver the respiratory gases to the patient 170. In some configurations, the tube system can be connected to the patient interface 160 to deliver the respiratory gases to the patient 170.

The tube system may comprise an inspiratory tube 140. The inspiratory tube 140 may be used to deliver the respiratory gases from the humidification apparatus 130 to the patient 170. In some configurations, multiple of the inspiratory tube 140 may be used to deliver respiratory gases to the patient 170.

In some embodiments, the tube system may comprise an expiratory tube 150. The expiratory tube 150 can be arranged and configured to remove exhaled gases from the patient 170. In some embodiments, the patient 170 may be at least partially within a controlled temperature environment 180.

Placement of Humidification Apparatus

FIGS. 2-4 and 7, are schematic views of example embodiments where the humidification apparatus 130 of the respiratory assistance system 100 may be positioned near the controlled temperature environment 180. By positioning the humidification apparatus 130 near or adjacent to the controlled temperature environment 180, the inspiratory tube 140 may be shorter than prior art tubes. In some such configurations, only one of the inspiratory tube 140 is used and the single inspiratory tube 140 may connect with the patient interface 160. The inspiratory tube 140 may be heated, such that a single heating zone may be achieved between the humidification apparatus 130 and the patient interface 160. As a result, the inspiratory tube 140 may not comprise an unheated region but may be heated along the full length of the inspiratory tube 140. In some configurations, the length of the inspiratory tube 140 between a connector used to connect the inspiratory tube to the humidification apparatus and a connector used to connect the inspiratory tube to the patient interface is heated. In some such configurations, the heater extends fully from a humidification apparatus connector to a patient end connector. In some configurations, the inspiratory tube 140 contains a heater that is positioned within the lumen of the inspiratory tube 140. In some configurations, the inspiratory tube 140 contains a heater that is positioned within a wall that defines the lumen of the inspiratory tube. In some configurations, the inspiratory tube 140 contains a heater that is positioned outside of the wall that defines the lumen of the inspiratory tube.

The humidification apparatus 130 may be positioned near to the controlled temperature environment 180. Such positioning exposes only a small region of the inspiratory tube 140 to the surrounding ambient environment. Such positioning results in a majority of the inspiratory tube 140 being positioned within the controlled temperature environment 180. This can be seen in more detail in FIG. 2, for example. The small region of the inspiratory tube 140 that is exposed to the surrounding ambient environment may have a reduced or minimised length relative to an overall length of the inspiratory tube 140. The minimised length may result in the humidified respiratory gases travelling over a shorter distance while exposed to the surrounding ambient environment. The short distance of travel may lead to reduced heat loss. In some embodiments, the short distance of travel outside of the controlled temperature environment 180 may reduce the condensate formation within the inspiratory tube 140. Reducing heat loss within the inspiratory tube 140 may allow a lower heater plate power or duty cycle to be used to heat the respiratory gases. In addition, by reducing heat loss in the region outside of the controlled temperature environment, the conduit can be controlled based upon the conditions inside of the controlled temperature environment with a reduced risk of condensation within the portion outside of the controlled temperature environment. In some embodiments, the travel distance between the humidification apparatus 130 and the controlled temperature environment 180 may be within a range of 0 mm to 1000 mm or 0 mm to 600 mm. As a result, some flexibility exists for the user during setup of the respiratory assistance system 100.

Figure 2:
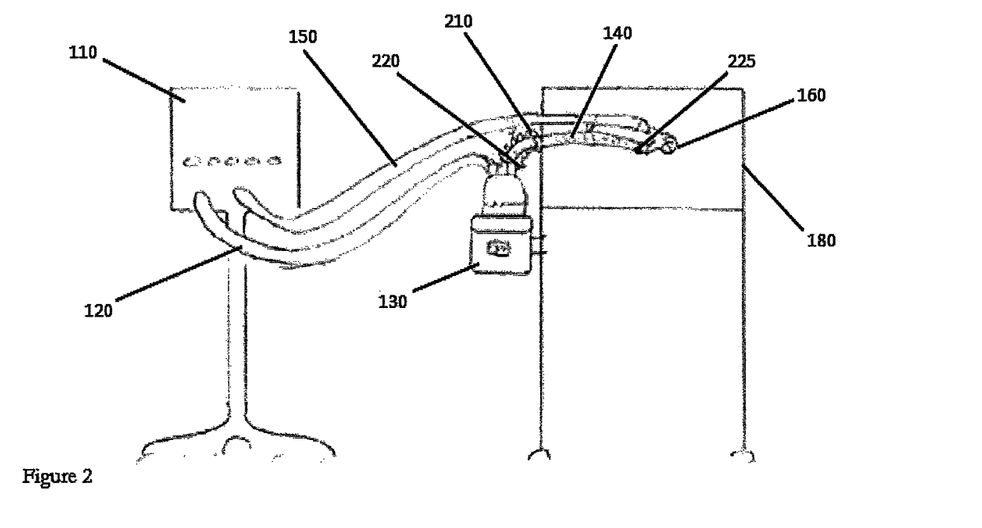
FIGS. 2-4 are schematic views of example embodiments of respiratory assistance systems configured for use with a controlled temperature environment as described according to the current disclosure.

In some embodiments, the length of the inspiratory tube 140 may be 500 mm to 600 mm. Thus, in some embodiments, the length of the inspiratory tube 140 may be 25% to 30% less than that of prior art inspiratory tubes, which may reduce the resistance to flow of the inspiratory tube 140. A shorter length of the inspiratory tube 140 may result in a reduced compressible volume in the respiratory assistance system 100. Compressible volume may refer to the volume of the system, which can be calculated as the volume between the gases source and the patient. Respiratory gases, such as air, are compressible, and, thus, reducing the compressible volume of the system may reduce the energy loss of the respiratory gases as they travel to the patient 170. As a result, the waveform of the respiratory gases delivered to the patient 170 may more closely resemble the waveform that was provided by the gases source 110. Thus, if the tube system comprises a low compressible volume, it may deliver to the patient 170 a waveform that better resembles the waveform intended for the patient 170. Increasing the distance between the humidification apparatus 130 and the controlled temperature environment 180 may increase the amount of condensate that is formed within the inspiratory tube 140, due to an increased exposure of the inspiratory tube 140 to the surrounding ambient environment.

In some embodiments, the length of the gases supply tube 120 may be increased to compensate for a reduced length of the inspiratory tube 140. For example, in some embodiments, the length of the gases supply tube 120 may be extended to a length of 1 m to 1.5 m. In some embodiments, an inversely proportional relationship may exist between the change in length of the gases supply tube 120 and the change in length of the inspiratory tube 140. For example, if the length of the inspiratory tube 140 decreases, the length of the gases supply tube 120 may increase, such that the overall volume may be maintained. This may enable the compressible volume to be similar to that of prior art systems and, thus, may maintain the waveform delivered to the patient 170 while reducing the condensate formed within the inspiratory tube 140, thereby improving usability of the respiratory assistance system 100.

Increasing the length of the gases supply tube 120 may also increase the flexibility of the respiratory assistance system 100. For example, the user may be able to move the humidification apparatus 130 more freely with regards to the gases source 110.

An increased length of the gases supply tube 120 may encourage greater temperature loss to the surrounding ambient environment along the length of the gases supply tube 120. A greater temperature difference between the temperature of the respiratory gases arriving at the humidification apparatus 130 and the temperature of the respiratory gases exiting the humidification apparatus 130 may facilitate greater transfer of humidity to the respiratory gases. If only a small temperature difference exists between the temperature of the respiratory gases arriving at the humidification apparatus 130 and the temperature of the respiratory gases exiting the humidification apparatus 130, less humidity may be transferred to the respiratory gases. Thus, the humidification apparatus 130, to increase the amount of humidity transferred to the respiratory gases, would need to provide supplementary heating to elevate the temperature of the respiratory gases as they exit the humidification apparatus 130. This supplementary heating may be in addition to the heating required to heat the respiratory gases to a desired temperature as they exit the humidification apparatus 130.

Increasing the length of the gases supply tube 120 may increase the temperature loss along the length of the gases supply tube 120. This may increase the temperature difference between the respiratory gases entering the humidification apparatus 130 and the respiratory gases exiting the humidification apparatus 130. As a result, the amount of supplementary heating supplied by the humidification apparatus 130 to humidify the respiratory gases may be reduced.

In some embodiments, it may be beneficial to maintain the temperature of the respiratory gases in the gases supply tube 120 such that it may reach the humidification apparatus 130 at a temperature that is no greater than, for example, 30° C. In some embodiments, the gases supply tube 120 may comprise a thermally conductive material such that additional heat loss to the surrounding ambient environment is encouraged.

In some embodiments, the inspiratory tube 140 may comprise a thermal insulation component 210 as shown in more detail in FIGS. 2 and 5-7. An example of the thermal insulation component 210 may be an insulating sleeve, cover, wrap or outer tube. In some embodiments, the thermal insulation component 210 may be added to the entire length of the inspiratory tube 140. In some embodiments, the thermal insulation component 210 may only be added to the region of the inspiratory tube 140 that may be exposed to the surrounding ambient environment. For example, the thermal insulation component 210 may be added to a first region of the inspiratory tube 140. A second region of the inspiratory tube 140 may be formed as the inspiratory tube 140 enters the controlled temperature environment 180 by crossing a periphery of the controlled temperature environment 180. In some embodiments, the second region of the inspiratory tube 140 may at least partially comprise the thermal insulation component 210. A periphery of the controlled temperature environment 180 as herein described may refer to a side of a housing, a wall, an edge or a boundary. The thermal insulation component 210 may further reduce condensate formation within the inspiratory tube 140. This may be especially desirable in the region of the inspiratory tube 140 that may be exposed to the surrounding ambient environment. Reducing heat loss to the surrounding ambient environment may also impact the rate of condensate formation within the inspiratory tube 140. In some configurations, the inspiratory tube 140 is constructed such that two or more distinct regions are defined with differing heat loss exhibited by two or more of those distinct regions.

Figure 5:
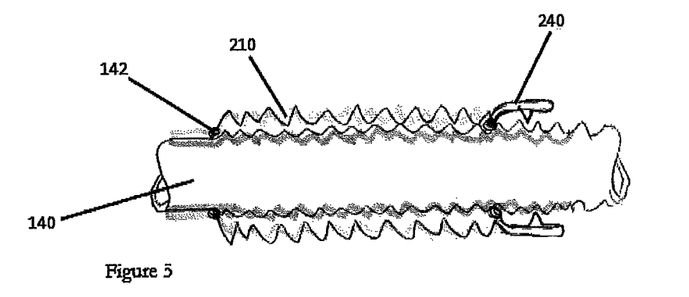
FIGS. 5-6 are perspective views of example embodiments of tube systems according to the current disclosure.

In some embodiments, the thermal insulation component 210 may comprise a sleeve. The sleeve 210 may be expandable or compressible in length to fit the distance between an outlet of the humidification apparatus 130 and an inlet to the controlled temperature environment 180. The sleeve may, for example, take the form of a concertina tube, which is shown in FIG. 5. As a result, the thermal insulation component 210 may be adaptable relative to the inspiratory tube 140 as desired depending on the position of the humidification apparatus 130 relative to the controlled temperature environment 180. The maximum extension length of the thermal insulation component 210 may correspond to the maximum length of the inspiratory tube 140 that may extend between the humidification apparatus 130 and the controlled temperature environment 180. In some embodiments, the thermal insulation component 210 may move freely along the length of the inspiratory tube 140. In some embodiments, the thermal insulation component 210 may be coupled to a first end 142 of the inspiratory tube 140. In some embodiments, the thermal insulation component 210 may be coupled to the first end 142 of the inspiratory tube 140 by a press fit or welding mechanism. In some embodiments, the thermal insulation component 210 may be releasably coupled to a second end 144 of the inspiratory tube 140. In some embodiments, the thermal insulation component 210 may be releasably coupled to the periphery of the controlled temperature environment 180. The releasable coupling may comprise, for example, a clipping mechanism. Thus, the thermal insulation component 210 may be a dynamic and adjustable insulating sleeve. The thermal insulation component 210 may be able to compensate for differences in user setup of the respiratory assistance system 100. Thus, if in some embodiments the respiratory assistance system 100 is set up such that a different length of the inspiratory tube 140 extends between the humidification apparatus 130 and the controlled temperature environment 180, the thermal insulation component 210 may be adjusted as desired to better fit the set up condition.

In some embodiments, the inspiratory tube 140 or the thermal insulation component 210 may be constructed from a thermally insulating material, for example, a plastic, a foamed material, or a material with good thermal insulation properties. In some embodiments, both the inspiratory tube 140 and the thermal insulation component 210 may be constructed from a thermally insulating material. In some embodiments, a combination of a thermally insulating material and the thermal insulation component 210 may be used to better manage condensate reduction within the inspiratory tube 140.

Figure 6:
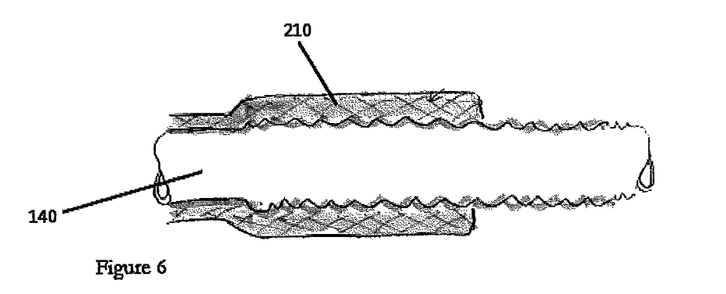

FIG. 6 is a perspective view of an embodiment wherein the thermal insulation component 210 comprises an overmolded material. Any suitable material can be used for the overmold. In some embodiments, the overmold may be formed from plastic or a foamed material. In some embodiments, a fluid gap 260 may exist between the inspiratory tube 140 and the thermal insulation component 210, as shown in more detail in FIG. 7. The fluid gap 260 may provide an additional layer of thermal insulation between the thermal insulation component 210 and the inspiratory tube 140. This additional layer of insulation may be provided by air that is captured within the fluid gap 260 providing an additional buffer between the inspiratory tube 140 and the thermal insulation component 210. In some embodiments, the air captured within the fluid gap 260 may be at least partially heated by the inspiratory tube 140. The fluid gap 260 may be configured to contain a volume of fluid, for example, gases such as air, or liquids such as water. Use of other gases or liquids may also fall within the scope of the disclosed apparatus and systems. In some embodiments, the thermal insulation component 210 may seal at the periphery of the controlled temperature environment 180 to reduce or eliminate the likelihood of fluid from the fluid gap 260 entering the controlled temperature environment 180. In some embodiments, the seal may be formed between the thermal insulation component 210 and the inspiratory tube 140. In some embodiments, the seal may be formed between the thermal insulation component 210 and the periphery of the controlled temperature environment 180. In some embodiments, the seal may take the form of a clipping mechanism, magnetic seal, adhesives, or a hook and loop mechanism. In some embodiments, additional layers of insulation, dynamic layers of insulation, or at least one part of the inspiratory tube 140 constructed from insulating materials may be used to provide additional insulation.

Figure 7:
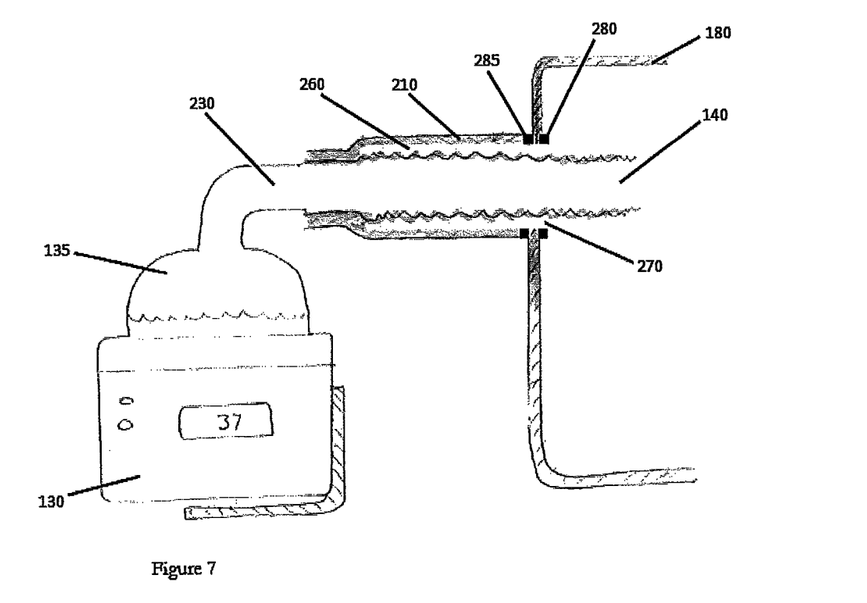
FIG. 7 is a schematic view of an example embodiment of a respiratory assistance system configured for use with a controlled temperature environment according to the current disclosure.

FIG. 7 is a schematic view of an example embodiment in which the volume of fluid within the fluid gap 260, which may be defined between the thermal insulation component 210 and the inspiratory tube 140, may be in fluid communication with the controlled temperature environment 180. An orifice 270 in a wall of the controlled temperature environment 180 may be configured to allow the inspiratory tube 140 access into the controlled temperature environment 180. In some embodiments, a coupling mechanism 240 may form a seal between the thermal insulation component 210 and the wall of the controlled temperature environment 180 such that they may be in fluid communication. As a result, the temperature of the fluid between the controlled temperature environment 180 and the thermal insulation component 210 may equilibrate or nearly equilibrate. In some embodiments, the temperature of the controlled temperature environment 180 may be higher than the temperature of the surrounding ambient environment. As a result, the fluid communication between the controlled temperature environment 180 and the thermal insulation component 210 may enable the fluid captured within the fluid gap 260 to maintain a temperature that is higher than that of the surrounding ambient environment. This may cause additional buffering of the inspiratory tube 140 from the surrounding ambient environment. Thus, heat loss from the inspiratory tube 140 may be reduced and condensate formation may be decreased.

With continued reference to FIG. 7, the coupling mechanism 240 may, in some embodiments, comprise a magnetic seal. A magnetic structure 280 may be positioned at the internal side of the wall at or near the orifice 270 of the controlled temperature environment 180. A corresponding magnetic structure 285 may be positioned on the thermal insulation component 210 at the second end 144 of the inspiratory tube 140. Interaction between the magnetic structure 280 and the corresponding magnetic structure 285 may couple the thermal insulation component 210 with the controlled temperature environment 180. In some embodiments, this interaction may form fluid communication between the components. In some embodiments, the magnetic structure 280 and the corresponding magnetic structure 285 may comprise a single magnet. In some embodiments, the magnetic structure 280 and the corresponding magnetic structure 285 may comprise multiple magnets. In some embodiments, the magnetic structure 280 and the corresponding magnetic structure 285 may each comprise a different number of magnets. In some embodiments, the shape of the magnetic structure 280 and the corresponding magnetic structure 285 may comprise for example, an annular ring, or may be circular or square. The magnetic structure 280 and the corresponding magnetic structure 285 are not limited to the aforementioned shapes, but may take the form of other shapes, which also fall within the scope of the disclosed apparatus and systems.

FIG. 5 is a view of an example embodiment wherein the thermal insulation component 210 and the inspiratory tube 140 are not separated by the fluid gap 260. The coupling mechanism 240 may provide a secure connection between the thermal insulation component 210 and the controlled temperature environment 180 to reduce the exposure of the inspiratory tube 140 to the surrounding ambient environment. The coupling mechanism 240, for example, may reduce or eliminate the likelihood of the thermal insulation component 210 slipping off or relaxing in use, which may leave a portion of the inspiratory tube 140 exposed to the surrounding ambient environment.

In some embodiments, the coupling mechanism 240 may comprise, for example, clips, adhesives, suction cups, or hook and loop mechanisms, to couple the thermal insulation component 210 with the periphery of the controlled temperature environment 180. In some embodiments, a friction fit may be used to enable the coupling. In some embodiments, the coupling mechanism 240 may be coupled to the thermal insulation component 210 and to the periphery of the controlled temperature environment 180 using, for example, adhesives, or hook and loop mechanisms. In some embodiments, the coupling mechanism 240 may be releasably coupled to the periphery of the controlled temperature environment 180. This may allow a user to use the respiratory assistance system 100 on different devices.

The coupling mechanism 240 may assist coupling of the humidification apparatus 130 to the periphery of the controlled temperature environment 180. In some embodiments, the coupling mechanism 240 may couple between an outlet port 230 of the humidification apparatus 130 and the inspiratory tube 140. In some embodiments, the inspiratory tube 140 may cross the periphery of the controlled temperature environment 180 to gain access to the controlled temperature environment 180. In some embodiments, the orifice 270 of the controlled temperature environment 180 may allow the inspiratory tube 140 access into the controlled temperature environment 180. The coupling mechanism 240 may seal the orifice 270. In some embodiments, the coupling mechanism 240 may comprise an electrical connector to facilitate electrical connection between the humidification apparatus 130 and the inspiratory tube 140. In some embodiments, the coupling mechanism 240 may comprise a probe or sensor port to be used for sensing a characteristic of the respiratory gases flow through the inspiratory tube 140. A characteristic of the respiratory gases flow may comprise for example, temperature, flow rate or humidity.

Figure 3:
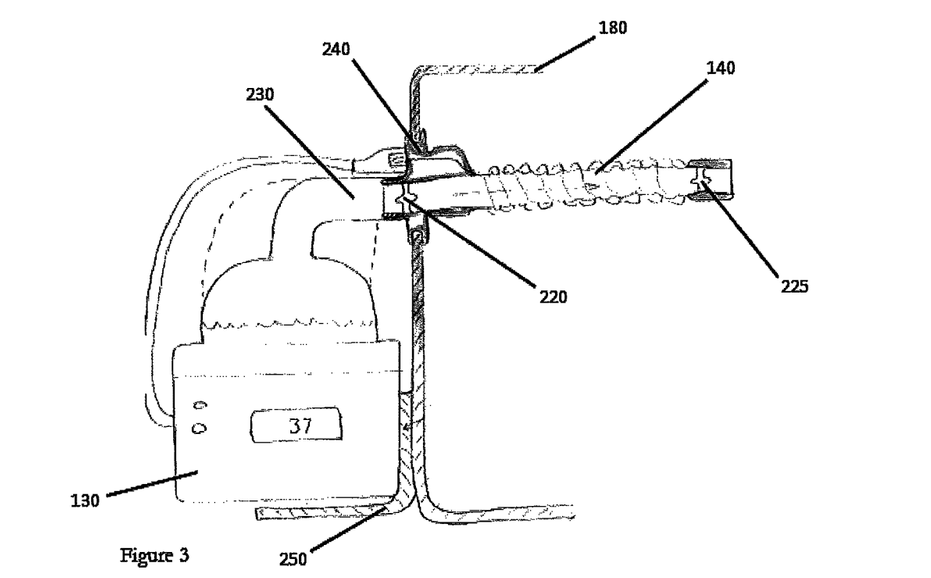
Figure 4:
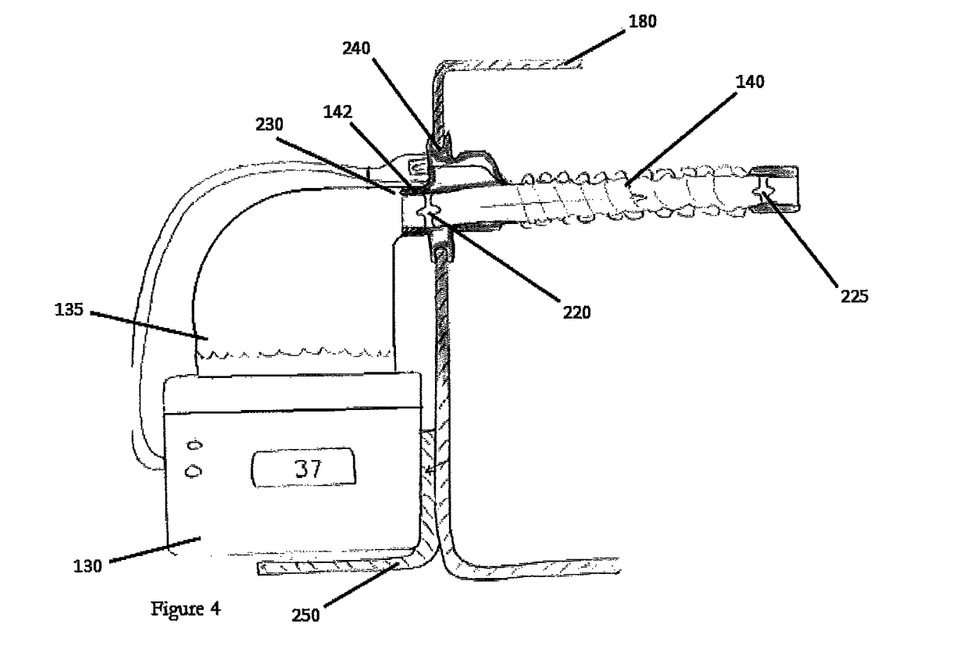

FIGS. 3-4 are schematic views of example embodiments of the humidification apparatus 130 comprising a sensor 220. In some embodiments, the sensor 220 may be configured to sense a characteristic of the respiratory gases flow for example, temperature, at the outlet port 230 of the humidification chamber 135 or, in some embodiments, at the first end 142 of the inspiratory tube 140. In some embodiments, the sensor 220 may be configured to sense characteristics of the respiratory gases flow, such as flow or humidity. Some embodiments may use other locations for sensing a characteristic of the respiratory gases flow, such as the heater plate, the junction between the inspiratory tube 140 and the humidification chamber 135 or at the inlet port of the humidification chamber 135. In some embodiments, a second sensor 225 may be located at the patient end of the inspiratory tube 140. In some embodiments, the second sensor 225 may be used to more accurately monitor and control the temperature of the respiratory gases. As a result, the heating of the inspiratory tube 140 may be controlled along the entire length of the tube such that the respiratory gases may be delivered to the patient 170 at a desired temperature and humidity level. In some embodiments, the controlled temperature environment 180 may contribute heat to the regions of the inspiratory tube 140 positioned within the controlled temperature environment 180. Thus, the second sensor 225 may further enable compensation of any additional heat by providing feedback to the control system of the humidification apparatus 130 regarding the temperature or other flow characteristic at the patient end of the inspiratory tube 140 such that the respiratory gases may be delivered at a desired temperature and humidity level.

The length of the inspiratory tube 140 that is exposed to the surrounding ambient environment may impact the amount of heat that the humidification apparatus 130 may be required to provide to heat the respiratory gases. The greater the exposed length of the inspiratory tube 140, the larger the anticipated heat losses to the surrounding ambient environment. As a result, it may become more difficult to control the temperature and humidity level of the respiratory gases that are delivered to the patient 170 at greater exposed lengths of the inspiratory tube 140. A shorter exposed length of the inspiratory tube 140 may provide better performance because it may be able to better compensate for changes in heating requirements due to the surrounding ambient environment.

In some embodiments, characteristics of the inspiratory tube 140, such as tube materials or compliance, may be considered. In some embodiments, tube compliance may impact energy absorption of the tube. For example, a more flexible or padded tube may absorb more energy, which may result in delivering a waveform to the patient that differs from the waveform leaving the ventilator.

As shown in FIGS. 3-4, some embodiments may comprise the humidification apparatus 130 coupled to the periphery of the controlled temperature environment 180. This may result in a minimal amount of the inspiratory tube 140 being exposed to the surrounding ambient environment. Coupling the humidification apparatus 130 to the periphery of the controlled temperature environment 180 may also reduce the cost of consumables for the respiratory assistance system 100. In some embodiments, the humidification apparatus 130 may be directly coupled with the periphery of the controlled temperature environment 180 such that none of the inspiratory tube 140 may be exposed to the surrounding ambient environment. Reduced exposure to the surrounding ambient environment may result in reduced condensate formation within the inspiratory tube 140. In some embodiments, the inspiratory tube 140 may have a shorter length, which may reduce user errors during setup of the respiratory assistance system 100.

In some embodiments, the outlet port 230 of the humidification chamber 135 may be configured to facilitate coupling with the inspiratory tube 140 at the periphery of the controlled temperature environment 180. In some embodiments, the outlet port 230 of the humidification chamber 135 can be configured to facilitate coupling with the orifice 270 of the controlled temperature environment 180. In some embodiments, the outlet port 230 of the humidification chamber 135 can be configured to facilitate coupling between the wall of the controlled temperature environment 180. In some embodiments, the outlet port 230 may comprise an elbow. In some embodiments, the outlet port 230 may comprise an engagement mechanism that is configured to releasably engage with the inspiratory tube 140. In some embodiments, the outlet port 230 may be configured to couple with the inspiratory tube 140 using a friction fit. The length of the outlet port 230 may be altered, for example, as shown in FIG. 4, wherein the length of the outlet port 230 is reduced. Reducing the length of the outlet port 230 may reduce the time that the characteristics of the respiratory gases can be influenced by the surrounding ambient environment. Thus, the embodiment shown in FIG. 4 may reduce condensate formation.

In some embodiments, a supporting structure 250, for example, a bracket, may be used to support the humidification apparatus 130 such that coupling is facilitated between the humidification apparatus 130 and the controlled temperature environment 180. The supporting structure 250 may comprise an attachment mechanism, such as clips, slidably engaging mechanisms, or support mechanisms, such as a tray or frame to facilitate coupling between the humidification apparatus 130 and the controlled temperature environment 180.

In some embodiments, the humidification chamber 135 may be shaped to encourage coupling with the controlled temperature environment 180. For example, as shown in FIG. 4, the humidification chamber 135 may comprise an altered shape such that the length of the outlet port 230 may be reduced. The humidification chamber 135 may comprise different shapes, structures or configurations, and such shapes, structures or configurations are within the scope of the disclosed apparatus and systems.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

Reference to any prior art in this specification is not, and should not be taken as, an acknowledgement or any form of suggestion that that prior art forms part of the common general knowledge in the field of endeavour in any country in the world.

The disclosed apparatus and systems may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the disclosed apparatus and systems and without diminishing its attendant advantages. For instance, various components may be repositioned as desired. It is therefore intended that such changes and modifications be included within the scope of the disclosed apparatus and systems. Moreover, not all of the features, aspects and advantages are necessarily required to practice the disclosed apparatus and systems. Accordingly, the scope of the disclosed apparatus and systems is intended to be defined only by the claims that follow.

What is claimed is:

1. A respiratory assistance system comprising:
a humidification apparatus configured to condition respiratory gases, the humidification apparatus comprising a humidification chamber configured to hold a volume of liquid; and
a tube system comprising a gases supply tube and an inspiratory tube,
the gases supply tube configured to extend between a gases source and the humidification apparatus, the gases supply tube being configured to transport respiratory gases from the gases source to the humidification apparatus,
the inspiratory tube comprising a tube wall defining a single lumen configured to transport the conditioned respiratory gases from the humidification apparatus to a patient, the tube wall defining an outermost wall of the inspiratory tube, at least a first region of the inspiratory tube configured to be at least partially positioned within a controlled temperature environment, and a second region of the inspiratory tube configured to be at least partially positioned outside of the controlled temperature environment and in a surrounding ambient environment,
wherein at least a portion of the second region of the inspiratory tube comprises a thermal insulating cover in contact with at least a portion of the tube wall and configured to insulate the inspiratory tube, wherein only the at least a portion of the second region is covered by the thermal insulating cover.

2. A respiratory assistance system as claimed in claim 1, wherein the thermal insulating cover is configured to insulate the entire second region of the inspiratory tube that is positioned outside of the controlled temperature environment.

3. A respiratory assistance system as claimed in claim 1, wherein the thermal insulating cover is configured to compress or expand in length to compensate for a change in length of the second region of the inspiratory tube.

4. A respiratory assistance system as claimed in claim 1, wherein the length of the gases supply tube is 1 meters 1.5 meters.

5. A respiratory assistance system as claimed in claim 1, wherein the length of the inspiratory tube is 500 millimeters to 600 millimeters.

6. A respiratory assistance system as claimed in claim 1, wherein the controlled temperature environment comprises a periphery and the humidification apparatus is coupled to the periphery of the controlled temperature environment.

7. A respiratory assistance system as claimed in claim 1, wherein the humidification chamber comprises a body and an outlet port that is configured to couple a first end of the inspiratory tube to the body of the humidification chamber, wherein the outlet port is directly connected to a perimeter wall of the body.

8. A respiratory assistance system as claimed in claim 1 further comprising a sensor configured to detect a characteristic of a respiratory gases flow.

9. A respiratory assistance system as claimed in claim 8, wherein the sensor is configured to detect a temperature of the respiratory gases flow.

10. A respiratory assistance system as claimed in claim 8, wherein the sensor is configured to detect a humidity of the respiratory gases flow.

11. A respiratory assistance system as claimed in claim 8, wherein the sensor is configured to detect a flow rate of the respiratory gases flow.

12. A respiratory assistance system as claimed in claim 8, wherein the inspiratory tube comprises a first end and a second end, the first end of the inspiratory tube being closer to an outlet port of the humidification chamber than the second end of the inspiratory tube, the sensor being located at one of the first end of the inspiratory tube or an outlet port of the humidification chamber of the humidification apparatus.

13. A respiratory assistance system as claimed in claim 12, further comprising a second sensor located at the second end of the inspiratory tube.

14. A respiratory assistance system as claimed in claim 1 wherein the thermal insulating cover comprises a concertina tube.

15. A respiratory assistance system as claimed in claim 1, wherein a fluid gap is between the thermal insulating cover and the inspiratory tube.

16. A respiratory assistance system as claimed in claim 1, wherein the controlled temperature environment comprises a periphery and the thermal insulating cover is configured to releasably couple with the periphery via a coupler.

17. A respiratory assistance system as claimed in claim 16, wherein the coupler comprises a magnetic structure.

18. A respiratory assistance system as claimed in claim 1, wherein the inspiratory tube is heated.

* * * * *

UNITED STATES PATENT AND TRADEMARK OFFICE
CERTIFICATE OF CORRECTION

PATENT NO. : 10,814,091 B2
APPLICATION NO. : 15/031191
DATED : October 27, 2020
INVENTOR(S) : Michael John Andresen Page 1 of 1

It is certified that error appears in the above-identified patent and that said Letters Patent is hereby corrected as shown below:

On the Title Page

In Column 1, item (71), Applicants, Line 2, after "Auckland (NZ);" delete "Natalie May Robertson, Auckland (NZ); Jonathan David Harwood, Auckland (NZ)".

In the Specification

In Column 6, Line 65, delete "endrotracheal" and insert --endotracheal--.

In the Claims

In Column 15, Lines 49-50, Claim 4, delete "1 meters 1.5 meters." and insert --1 meters-1.5 meters.--.

Signed and Sealed this
Twelfth Day of January, 2021

Andrei Iancu
*Director of the United States Patent and Trademark Office*